United States Patent
Machida

[11] Patent Number: 5,897,499
[45] Date of Patent: Apr. 27, 1999

[54] ULTRASONIC DIAGNOSTIC APPARATUS FOR CURSOR CONTROL

[75] Inventor: Etsuro Machida, Kawasaki, Japan

[73] Assignee: Fujitsu Limited, Kawasaki, Japan

[21] Appl. No.: 08/821,568

[22] Filed: Mar. 19, 1997

[30] Foreign Application Priority Data

Sep. 30, 1996 [JP] Japan .................................. 8-259303

[51] Int. Cl.⁶ .................................................. A61B 8/00
[52] U.S. Cl. ............................................................ 600/443
[58] Field of Search .............................. 128/660.5, 660.4, 128/916, 661.04, 662.01, 660, 663, 661.07

[56] References Cited

U.S. PATENT DOCUMENTS

| | | | |
|---|---|---|---|
| 4,501,277 | 2/1985 | Hongo | 128/660 |
| 5,285,788 | 2/1994 | Arenson et al. | 128/660.05 |
| 5,425,365 | 6/1995 | Iinuma | 128/660.05 |
| 5,538,003 | 7/1996 | Gadonniex et al. | 128/660.09 |
| 5,562,097 | 10/1996 | Yao | 128/662.01 |
| 5,568,812 | 10/1996 | Murashita et al. | 128/660.04 |

*Primary Examiner*—Marvin M. Lateef
*Assistant Examiner*—Maulin Patel
*Attorney, Agent, or Firm*—Staas & Halsey

[57] ABSTRACT

An ultrasonic diagnostic apparatus has a function capable of performing a cursor display suitable to a feeling of handling. A cursor is permitted to move to not only a position in the noticed area on a two-dimensional image, but also to another position. When the cursor moves to the another position, an available area closest to the position of the cursor shifted is selected as the noticed area.

10 Claims, 12 Drawing Sheets

ULTRASONIC DIAGNOSTIC APPARATUS FOR CURSOR CONTROL

BACKGROUND OF THE INVENTION

1. Field of the Invention

The present invention relates to an ultrasonic diagnostic apparatus. In particular, the present invention relates to an ultrasonic diagnostic apparatus wherein ultrasounds are transmitted in a direction along a scan line extending within a subject and ultrasounds reflected on the respective points on the scan line are received to form received signals is sequentially repeated on a plurality of scan. Thereby, in the present invention, an image signal carrying image information on a tomographic plane formed by the plurality of scan lines inside the subject is produced on the basis of the received signals derived through those operations, and a two-dimensional image based on the image signal thus derived is displayed.

2. Description of the Related Art

Hitherto, there has been used an ultrasonic diagnostic apparatus for diagnosis of diseases of viscus inner organs or the like within a subject, and particularly, within a human. Such a device has operated by means of producing and displaying a tomographic image of the inside of the human body and a blood flow distribution image on the tomographic plane on the basis of received signals derived through transmission and reception of ultrasounds with respect to the subject.

In such an ultrasonic diagnostic system, for example, there are displayed two-dimensional images such as the above-mentioned tomographic image and blood flow distribution image, and in addition a cursor superposed on the two-dimensional images. In some case, it happens that there is a need to move the cursor on a screen through operations of a handler, for example, a track ball, a mouse and the. Such a movement is needed, for example, to select one among a plurality of scan lines appearing on the two-dimensional image, or select one among a plurality of areas which are formed on each of the plurality of scan lines in such a manner that the respective scan line is divided into a plurality of partitions.

Hereinafter, in a case where one scan line is selected from among several of scan lines, the selected scan line is referred to as a "noticed area". Each of a plurality of scan lines, which are possible to be selected in the form of the noticed area, is hereinafter referred to as a "processing unit area". On the other hand, in a case where each of a plurality of scan lines is divided into a plurality of areas, and one area is selected from among the thus divided plurality of areas, the selected area is referred to as a "noticed area", and each of a plurality of areas, which are possible to be selected as the noticed area, is referred to as a "processing unit area".

As a case in which it is necessary to designate a noticed area from among a plurality of processing unit areas, for example, there are considered the following cases. One is that a two-dimensional image representative of a tomographic image or a two-dimensional image representative of a blood flow distribution image is displayed, and a predetermined point (noticed area) of the displayed two-dimensional image is designated so as to observe changes with time of a blood flow in the designated noticed area. Another is that a two-dimensional image representative of a tomographic image is displayed, and one scan line (noticed area) of a plurality of scan lines constituting the two-dimensional image is designated so as to observe changes with time of a one-dimensional ultrasonic reflection intensity distribution (boundary site of internal organs or the like) in the designated noticed area (one scan line).

By the way, a plurality of scan lines on a two-dimensional image have discrete intervals between adjacent scan lines. Also in a case of setting up a plural of processing unit areas possible to be designated on one scan line as the noticed area, those plurality of processing unit areas are set up at discrete sites on the one scan line.

Consequently, when the noticed area is designated by the cursor (from among such discrete processing unit areas), as a display position of the cursor, there is permitted only a position superposed on any of the processing unit areas.

However, if the display position of the cursor is permitted to be only a position superposed on any of the processing unit areas, then this causes an intermittent movement of the cursor on a display screen. Thus the movement of the cursor is not synchronized with an operation of the handler. Thus, there arises the problem that an operator will experience a sense of incongruity. Specifically, for example, in case of a sector scan, the scan lines are close near the surface of the human body (as the subject), while the scan lines are scattered at a site the deep within the subject. In this case, when it is intended to move the cursor to another scan line, a movement of the cursor will be different, in spite of the same operation of the handler. That is, the cursor movement will differ between a case in which the cursor is located in an area corresponding to an area near the surface of the human body (as the subject) within the subject and a case in which the cursor is located within an area corresponding to an area deep within the subject. This causes an operator to experience a sense of great incongruity.

SUMMARY OF THE INVENTION

In view of the foregoing, it is therefore an object of the present invention to provide an ultrasonic diagnostic apparatus having a function capable of performing a cursor display suitable to a feeling of handling.

To achieve the above-mentioned object, according to the present invention, there is provided an ultrasonic diagnostic apparatus comprising:

(1) an ultrasonic transmitter-receiver means wherein an operation in which ultrasounds are transmitted in a direction along a scan line extending within a subject and ultrasounds reflected on the respective points on the scan line are received to form received signals is sequentially repeated on a plurality of scan lines;

(2) an image forming means for generating an image signal carrying image information on a tomographic plane within the subject in accordance with the received signals, said tomographic plane being formed by the plurality of scan lines;

(3) an image display means, having a display screen on which images are displayed, for displaying on said display screen a two-dimensional image based on said image signal;

(4) a processing control means for selecting a noticed area in form of a processing unit area from among a plurality of processing unit areas each corresponding to an associated one of said plurality of scan lines or from among a plurality of processing unit areas or domains in each of which the associated one of said plurality of scan lines is partitioned into a plurality of segments, and for causing at least one of said ultrasonic transmitter-receiver means, said image forming means and said image display means to carry out a processing according to the selected noticed area;

(5) a cursor display control means for providing such a control that a cursor for designating the noticed area from among said processing unit areas is displayed on the display screen of said display means; and (6) a handler for performing an indication input of a display position of the cursor on the display screen of said display means, wherein said cursor display control means (5) permits the cursor on the display screen to be displayed freely at any position including a position superposed on any one of said processing unit areas on the two-dimensional image displayed on the display screen and also including a position out of any processing unit areas, in accordance with an operation of said handler, and wherein said processing control means (4) selects as the noticed area the processing unit area close to a position in which the cursor is displayed.

According to the ultrasonic diagnostic apparatus of the present invention, a cursor is permitted to be displayed at not only a position in which the cursor is superposed on processing unit areas on a two-dimensional image, but also a position out of the processing unit areas. This feature makes it possible to move smoothly the cursor to a position according to the operation of the handler, thereby obtaining a movement of the cursor suitable to a feeling of the operation of the handler. In this case, however, there will arise such a problem that a cursor is shifted to a position in which the cursor is not superposed on any processing unit area, as a result, any processing unit area is not designated as a noticed area. According to the present invention, this problem has been solved by means of selecting as the noticed area the processing unit area close to the position at which the cursor is displayed.

In the ultrasonic diagnostic apparatus as mentioned above, it is preferable that said processing control means (4) provides such a control that while said handler is operated and the cursor travels on the display screen, the noticed area is maintained before an operation of said handler, and at a time point when the operation is terminated and the cursor on the display screen is stopped, a new noticed area is selected. In this case, it is acceptable that said cursor display control means (5) permits the cursor on the display screen to be shifted to a position superposed on a selected noticed area when said processing control means select the noticed area.

According to the prior art, during a movement of the cursor, different processing unit areas are sequentially designated as a noticed area. Thus, it is difficult during a movement of the cursor to obtain images representative of changes with time of blood flow of a fixed noticed area and internal organs. This arises a problem such that meaningless images due to a sequential movement of noticed areas is displayed and is troublesome. According to the present invention, this problem has been solved by means of selecting a new noticed area when the cursor is stopped.

Further, in the ultrasonic diagnostic apparatus as mentioned above, it is preferable that said cursor display control means (5) permits the cursor on the display screen to be displayed freely at any position including a position superposed on any one of said processing unit areas on the two-dimensional image displayed on the display screen, a position out of any processing unit areas on the two-dimensional image, and also a position out of the display area on the two-dimensional image, in accordance with an operation of said handler, and wherein said processing control means (4) provides such a control that while said handler is operated and the cursor on the display screen is displayed at the position out of the display area on the two-dimensional image, the noticed area associated with a display of the cursor within the display area on the two-dimensional image is maintained, and after the cursor on the display screen shifts into the display area on the two-dimensional image, a new noticed area is selected.

Furthermore, in the ultrasonic diagnostic apparatus as mentioned above, it is preferable that in the event that a cursor for selecting a noticed area from among the processing unit areas in which each of the plurality of scan lines is partitioned into a plurality of segments is displayed within a predetermined shallow area, corresponding to a shallow portion of the subject, on the two-dimensional image displayed on the display screen, when said handler is operated to move the cursor in a direction traversing the scan lines, said cursor display control means (5) moves the cursor in turn every operation to a position in which the cursor is superposed on an adjacent scan line, regardless of an amount of operation of the cursor.

The present invention is applicable to a various type of ultrasonic diagnostic apparatuses. For example, in the ultrasonic diagnostic apparatus according to the present invention, it is acceptable that said image forming means (2) produces in addition to the two-dimensional image a Doppler image representative of variations with time of a blood flow on a noticed area selected, from among the processing unit areas in which each of the plurality of scan lines is partitioned into a plurality of segments, by said processing control means, in accordance with the received signals, and said image display means (3) displays on said display screen the Doppler image instead of the two-dimensional image, or in parallel with the two-dimensional image.

In the ultrasonic diagnostic apparatus according to the present invention, alternatively, it is acceptable that said image forming means (2) produces in addition to the two-dimensional image an M-mode image representative of variations with time of a one-dimensional ultrasounds reflection intensity distribution on a noticed area associated with a single scan line selected from among the processing unit areas each corresponding to an associated one of said plurality of scan lines, by said processing control means, in accordance with the received signals, and said image display means (3) displays on said display screen the M-mode image instead of the two-dimensional image, or in parallel with the two-dimensional image.

In the ultrasonic diagnostic apparatus according to the present invention, alternatively, it is acceptable that said image forming means (2) produces in addition to the two-dimensional image a color M-mode image representative of variations with time of a one-dimensional blood flow distribution on a noticed area associated with a single scan line selected from among the processing unit areas each corresponding to an associated one of said plurality of scan lines, by said processing control means, in accordance with the received signals, and said image display means (3) displays on said display screen the color M-mode image instead of the two-dimensional image, or in parallel with the two-dimensional image.

In the ultrasonic diagnostic apparatus according to the present invention, alternatively, it is acceptable that said image forming means (2) produces in addition to the two-dimensional image a CWD image representative of variations with time of an average blood flow on a noticed area associated with a single scan line selected from among the processing unit areas each corresponding to an associated one of said plurality of scan lines, by said processing control means, in accordance with the received signals, and said image display means (3) displays on said display screen the CWD image instead of the two-dimensional image, or in parallel with the two-dimensional image.

Finally, in the ultrasonic diagnostic apparatus according to the present invention, it is acceptable that said ultrasonic transmitter-receiver means (1) transmits and receives ultrasounds to form a focus in a noticed area selected, from among the processing unit areas in which each of the plurality of scan lines is partitioned into a plurality of segments, by said processing control means.

DESCRIPTION OF THE PREFERRED EMBODIMENTS

Hereinafter, there will be described embodiments of the present invention.

Figure 1:
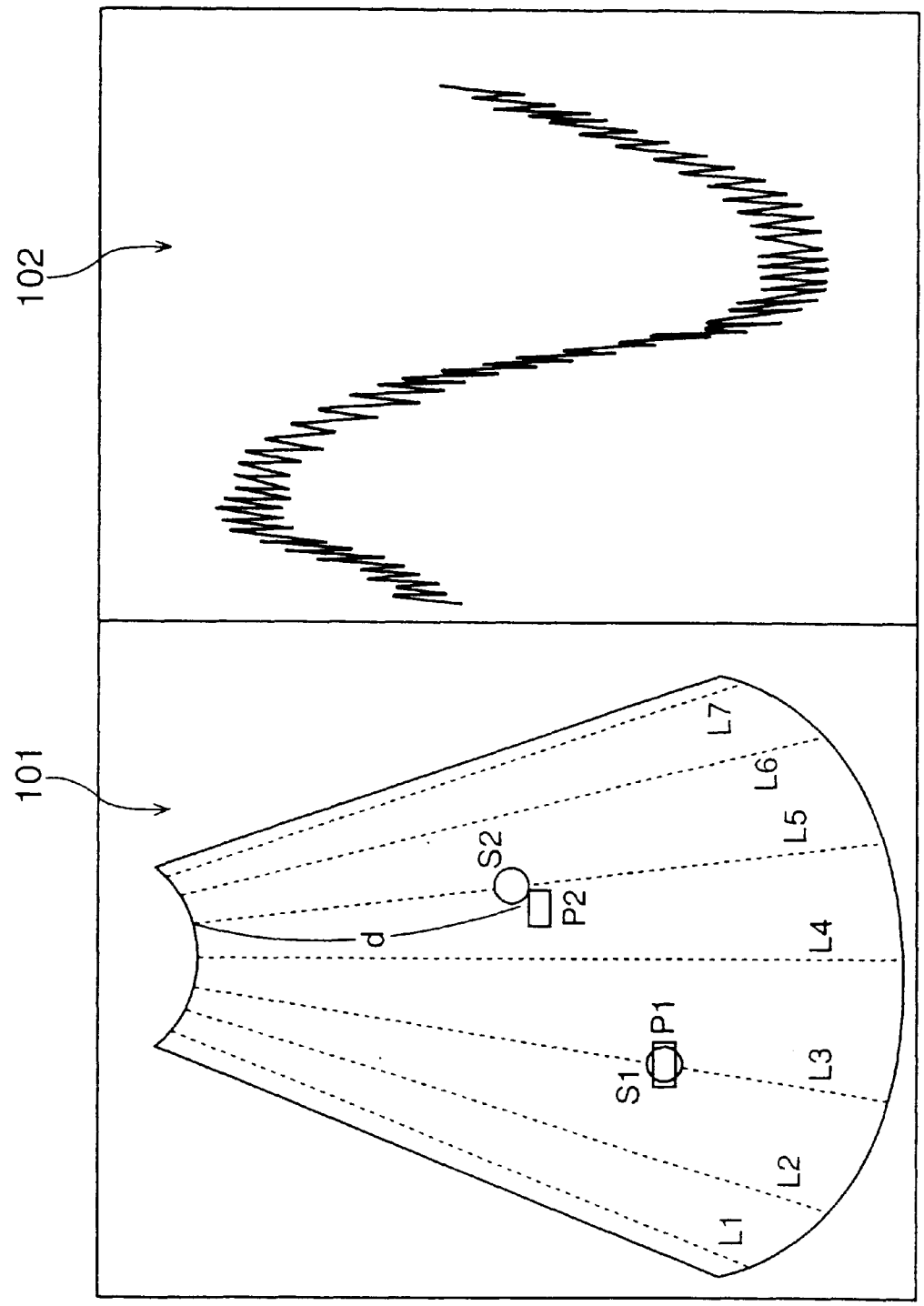
FIG. 1 is an illustration showing, by way of example, images displayed on a display screen, for the purpose of explanation of first to third embodiments of an ultrasonic diagnostic apparatus according to the present invention.

FIG. 1 is an illustration showing, by way of example, images displayed on a display screen, for the purpose of explanation of first to third embodiments of an ultrasonic diagnostic apparatus according to the present invention.

On the display screen shown in FIG. 1, there are displayed in parallel a black and white tomographic image 101 and a so-called Doppler image 102. The tomographic image 101 is representative of an ultrasound reflection intensity distribution on a predetermined tomographic plane within the subject. In the so-called Doppler image 102, direction and magnitude of blood flow at a predetermined sample position within the tomographic image 101 are expressed on a vertical axis, and changes with time of the blood flow are expressed on a horizontal axis. The Doppler image 102 is sequentially scrolled with the passage of time. According to this example, the tomographic image 101 corresponds to the two-dimensional image referred to in the present invention, and the sample position corresponds to the noticed area referred to in the present invention.

The tomographic image 101 is illustrated with only seven scan lines L1 to L7 for the purpose of avoiding complicated illustration. Further, for the purpose of easy comprehension of the tomographic image 101, there are shown sample positions S1 and S2 before and after movement, and Doppler sample markers P1 and P2 before and after movement. Here, the Doppler sample marker corresponds to the cursor referred to in the present invention. In FIG. 1, in the tomographic image 101, there are displayed two sample positions S1 and S2 and two Doppler sample markers P1 and P2. It is noted, however, that actually the sample positions S1 and S2 are not objects of display on a direct basis, and only one Doppler sample marker is displayed. With respect to the sample positions, there are set up a plurality of sample positions on each of the plurality of scan lines L1 to L7.

In this example, the sample position before a movement is located at the sample position S1, and the Doppler sample marker P1 is displayed at the same position as the sample position S1. Now it is assumed that the Doppler sample marker P1 is shifted to the position of the Doppler sample marker P2. At that time, the sample position shifts from the sample position S1 to the sample position S2 closest to the Doppler sample marker P2.

In this case, as shown in the second embodiment which will be described later, it is preferable that the sample position is fixed on the sample position S1 before a movement while the Doppler sample marker travels. When the Doppler sample marker stops at the position of the Doppler sample marker P2, then the sample position shifts from the sample position S1 (before a movement) to the sample position S2 (after the movement). In this case, during a movement of the Doppler sample marker there is displayed, as the Doppler image 102, a scroll image representative of blood flow information on the sample position S1 before the movement. After the termination of movement of the Doppler sample marker, there is displayed a scroll image representative of blood flow information on the sample position S2 after the movement.

Further, in this case, as shown in FIG. 1, after the movement the Doppler sample marker P2 is continued to be displayed at the position of the sample position S2 after the movement. Then, as shown in the third embodiment (to be described later), it is acceptable that, after the Doppler sample marker stops at the position of the Doppler sample marker P2 and the sample position moves to the sample position S2, the Doppler sample marker is shifted to a position at which the Doppler sample marker is superposed on the sample position S2.

It is acceptable to display a so-called color flow imaging picture showing a blood flow distribution (on a tomographic plane or a part of areas of the tomographic plane), which is superposed on the black and white tomographic image 101. In such a color flow imaging picture, the blood flow distribution is indicated in such a manner that a blood flow of direction toward the surface (upper end of the tomographic image 101 shown in FIG. 1) and blood flow in the direction away from the surface are displayed with red and blue, respectively. In such a case, the blood flow velocity at each of the pixels is displayed with color density (luminance) of the thus given red and blue. This feature makes it possible to simultaneously display an overall blood flow distribution and the Doppler image 102 representative of detailed blood flow information as to the sample position. This aspect is applicable to the respective embodiments which will be described hereinafter.

Figure 2:
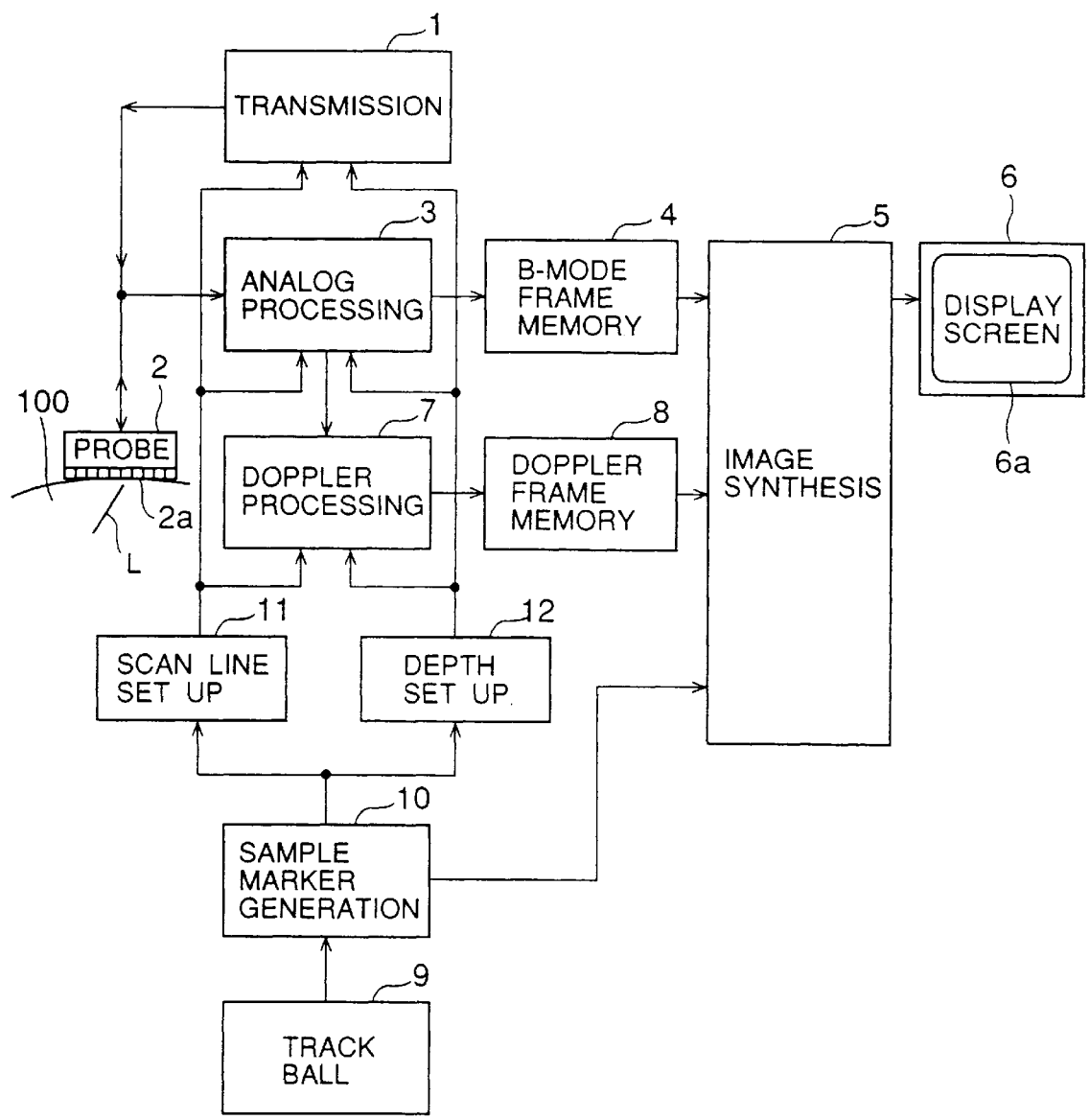
FIG. 2 is a block diagram of an ultrasonic diagnostic apparatus according to the first embodiment of the present invention.

FIG. 2 is a block diagram of an ultrasonic diagnostic apparatus according to the first embodiment of the present invention.

A transmission unit 1 produces signals for an ultrasound transmission and supplies the signals to a probe 2 having a plurality of piezo-electric transducers 2a arranged on the tip thereof. The piezo-electric transducers 2a transmit ultrasounds in a direction along a piece of scan line L within a subject 100. A transmission direction of ultrasounds, or a direction of the scan line L, is determined by the signals produced by the transmission block 1 and applied to the plurality of piezo-electric transducers 2a.

Ultrasounds reflected within the subject 100 and returned to the probe 2 are received by the probe 2 to be converted into electrical received signals. The thus formed received signals are fed to an analog processing unit 3. The analog processing unit 3 performs a so-called beamforming in which a plurality of signals derived from the plurality of piezo-electric transducers 2a of the probe 2 are mutually delayed and added to one another, thereby producing signals carrying one-dimensional information along the scan line L extending within the subject 100. The analog processing unit 3 further performs a detection to produce an image signal defined by the envelop of the obtained signal. The image signal thus produced is converted into a digital signal and then fed to a B-mode frame memory 4. The B-mode frame memory 4 stores the one-dimensional image signal transmitted from the analog processing unit 3.

In this manner, transmission and reception of ultrasounds is sequentially repeatedly performed on a plurality of directions (e.g. 128) of scan lines L included in a predetermined tomographic plane within the subject 100, so that the B-mode frame memory 4 stores an image (a so-called B-mode image) representative of a two-dimensional ultrasonic reflection intensity distribution on the tomographic plane formed by the plurality of scan lines within the subject 100. When the B-mode frame memory 4 stores a frame of image signal (corresponding to a sheet of two-dimensional image), the image signal is read out from the B-mode frame memory 4 and synthesized with another image by an image synthesizer unit 5. The thus synthesized image by the image synthesizer unit 5 is fed to an image display unit 6 in which images including the B-mode image are displayed on a display screen 6a.

A Doppler processing unit 7 receives directly a signal subjected to the beamforming process by the analog processing unit 3. Upon receipt of the signal subjected to the beamforming process, the Doppler processing unit 7 produces a Doppler signal representative of direction and velocity of a blood flow of a sample position within the subject 100 on the basis of a Doppler frequency shift occurred on the reflection ultrasounds reflected on the sample position owing to the blood flow of the sample position. With respect to the designation of the sample position, it will be described later. The Doppler signal thus produced is stored in a Doppler frame memory 8. When the Doppler processing unit 7 produces the Doppler signal, transmission and reception of ultrasounds is repeatedly performed in a direction from the probe 2 to the sample position with higher frequency as compared with another direction within the tomographic plane. Thus, the Doppler processing unit 7 can find blood flow information on the sample position with greater accuracy on the basis of the signals obtained through a great number of times of transmission and reception of ultrasounds on the sample position.

The Doppler signal stored in the Doppler frame memory 8 is read out and fed via the image synthesizer unit 5 to the image display unit 6. In the image display unit 6, the Doppler signal is displayed on the display screen 6a in the form of the Doppler image 102 as shown in FIG. 1 standing side by side with the tomographic image 101.

Next, there will be described a way of setting up or designation of the sample position.

The ultrasonic diagnostic apparatus has a track ball 9, which is a one type of the handler referred to in the present invention, for generating shift data representative of movement of an X direction (horizontal direction) and a Y direction (vertical direction) on the display screen 6a of the Doppler sample marker to be displayed on the display screen 6a, in accordance with an operation. The shift data generated through the operation of the track ball 9 is fed to a sample marker generation unit 10, which is an example of cursor display control means referred to in the present invention, for evaluating coordinates to be newly displayed on the display screen 6a as to the Doppler sample marker on the basis of the shift data inputted from the track ball 9 to generate a figure of the Doppler sample marker to be displayed at the coordinates. The figure of the Doppler sample marker thus generated is fed to the image synthesizer unit 5. The indication coordinates of the Doppler sample marker is not restricted to only the coordinates of the position at which the Doppler sample marker is superposed on the sample position, and is freely selectable as far as the display area of the tomographic image 101 (FIG. 1) is concerned.

The image synthesizer unit 5 transmits the figure of the Doppler sample marker to the display unit 6 superposing the same on the B-mode image read out from the B-mode frame memory 4. The display unit 6 displays on the display screen 6a the Doppler sample marker superposed on the B-mode image. The sample marker generation unit 10 outputs the indication coordinates of the Doppler sample marker, which is fed to a scan line set up unit 11 and a depth set up unit 12. The scan line set up unit 11 and the depth set up unit 12, taking in their combination, correspond to processing control means referred to in the present invention. The scan line set up unit 11 selects the scan line closest to the indication coordinates in accordance with indication coordinates information of the Doppler sample marker transmitted from the sample marker generation unit 10. On the other hand, the depth set up unit 12 sets up a depth (depth d shown in FIG. 1) of the sample position in accordance with indication coordinates information of the Doppler sample marker transmitted from the sample marker generation unit 10. That is, the sample position is selected in accordance with the scan line and the depth selected and set up by the scan line set up unit 11 and the depth set up unit 12, respectively. Information as to the scan line and the depth obtained by the scan line set up unit 11 and the depth set up unit 12 is fed to the transmission unit 1, the analog processing unit 3 and the Doppler processing unit 7. The transmission unit 1, the analog processing unit 3 and the Doppler processing unit 7 perform reception of ultrasounds and beamforming processing for obtaining the B-mode image, and in addition perform transmission of ultrasounds, a beamforming processing and a Doppler processing so as to obtain a Doppler image on the selected sample position.

Figure 3:
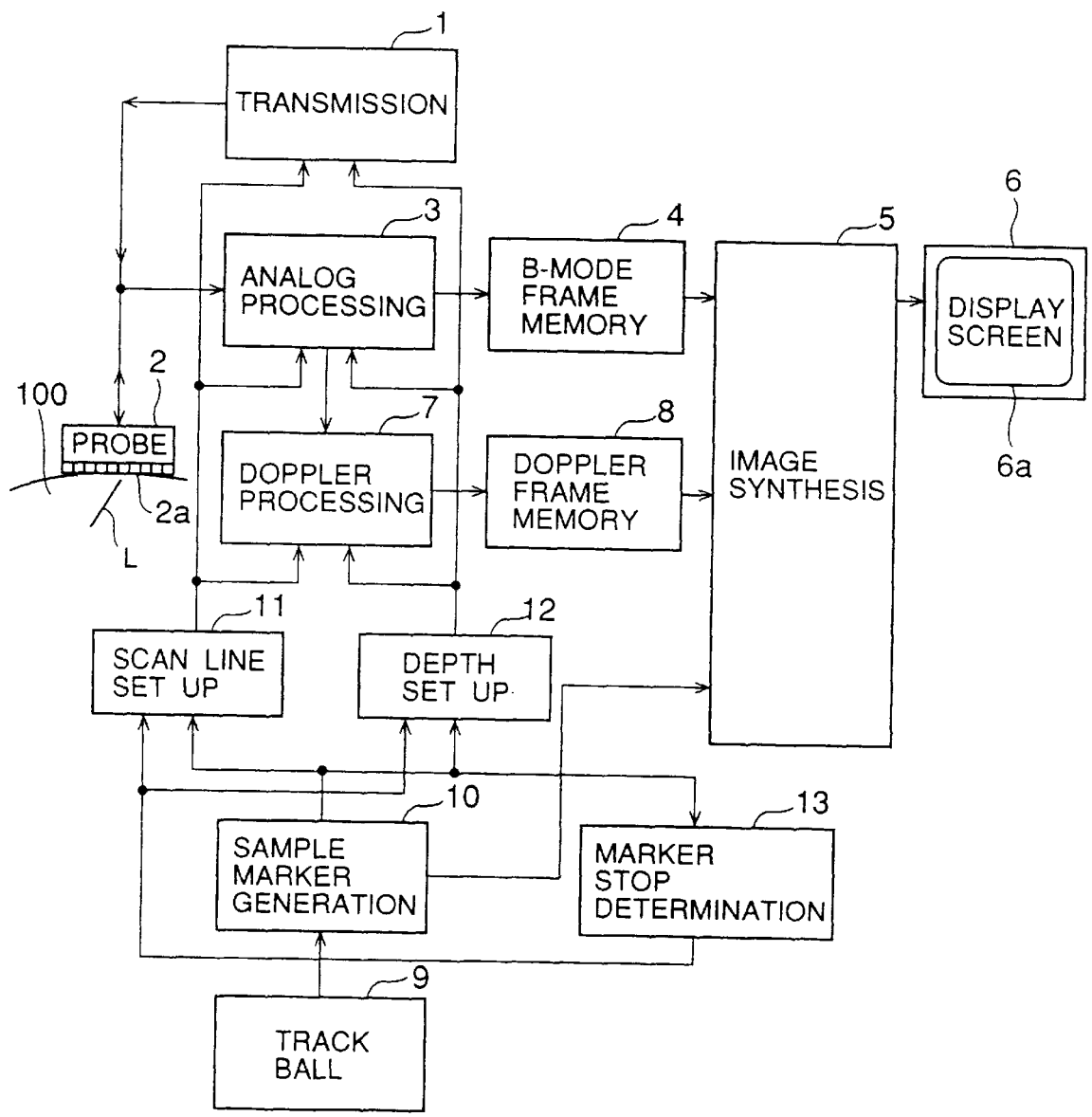
FIG. 3 is a block diagram of an ultrasonic diagnostic apparatus according to the second embodiment of the present invention.

FIG. 3 is a block diagram of an ultrasonic diagnostic apparatus according to the second embodiment of the present invention. The difference of the second embodiment from the first embodiment shown in FIG. 2 will be described hereinafter. In the following figures, the same parts are denoted by the same reference numbers as those of FIG. 2.

In the second embodiment shown in FIG. 3, as compared with the first embodiment shown in FIG. 2, there is provided a maker stop determination unit 13. The maker stop determination unit 13 receives the indication coordinates of the Doppler sample marker outputted from the sample marker generation unit 10. Upon receipt of the indication coordinates, the maker stop determination unit 13 monitors changes of the indication coordinates and determines that the Doppler sample marker stops in travelling when the indication coordinates does not vary for a limited time. The maker stop determination unit 13 outputs a signal indicating whether the Doppler sample marker is in travelling (the track ball 9 is being operated) or is stopped (the track ball 9 is terminated in operation). This signal is fed to the scan line set up unit 11 and the depth set up unit 12. The scan line set up unit 11 and the depth set up unit 12 maintain respectively the previous scan line number and depth during an application of the signal indicating that the Doppler sample marker is in travelling. When the scan line set up unit 11 and the depth set up unit 12 receives from the maker stop determination unit 13 the signal indicating that the Doppler sample marker is stopped in travelling, the scan line set up unit 11 and the depth set up unit 12 evaluate respectively scan line number and depth for designating a new sample position in accordance with the indication coordinates of the Doppler sample marker which is received from the sample marker generation unit 10 at that time. However, the sample marker generation unit 10 continues to transmit to the image synthesizer unit 5 the signal representative of the figure of the Doppler sample marker, regardless of the operation of the maker stop determination unit 13, even while the track ball 9 operated. In other words, when the track ball 9 is operated, the Doppler sample marker travels on the display screen 6a following an operation of the track ball 9, but a change of the sample position is carried out after the termination of the operation of the track ball 9.

Figure 4:
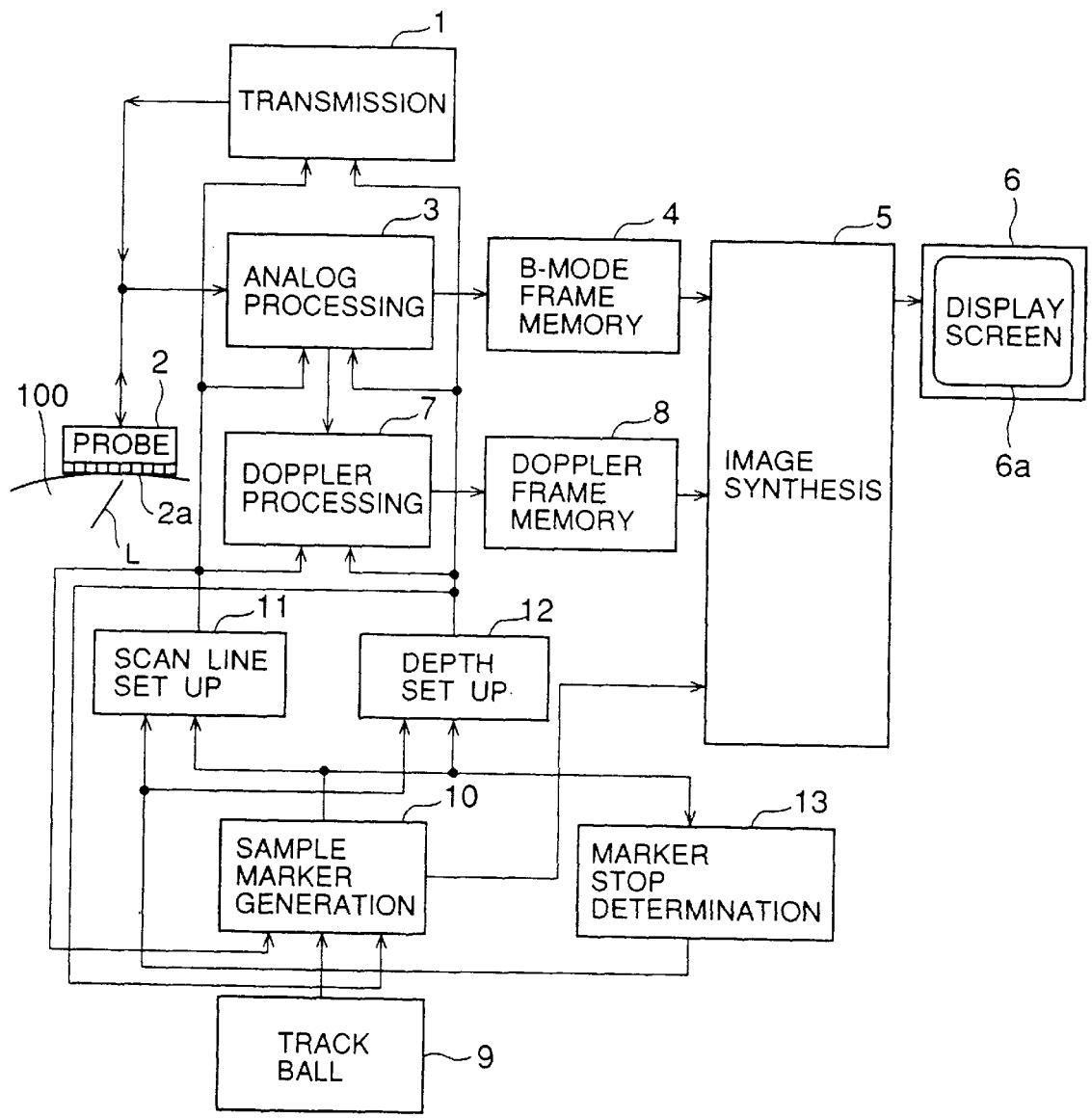
FIG. 4 is a block diagram of an ultrasonic diagnostic apparatus according to the third embodiment of the present invention.

FIG. 4 is a block diagram of an ultrasonic diagnostic apparatus according to the third embodiment of the present invention. The difference of the third embodiment from the second embodiment shown in FIG. 3 will be described hereinafter.

Upon receipt of detection of the stop (termination of the operation of the track ball 9) of the Doppler sample marker by the maker stop determination unit 13, when the scan line set up unit 11 and the depth set up unit 12 determines a new sample position (scan line number and depth) in accordance with the indication coordinates of the Doppler sample marker received from the sample marker generation unit 10 at that time, the signal representative of the new sample position (scan line number and depth) is fed also to the sample marker generation unit 10. Upon receipt of such a signal representative of the new sample position, the sample marker generation unit 10 updates the Doppler sample marker at the position in which the Doppler sample marker is superposed on the sample position indicated by the signal received. This feature makes it possible to avoid such a situation that the Doppler sample marker is continued to be displayed out of the sample position.

Figure 5:
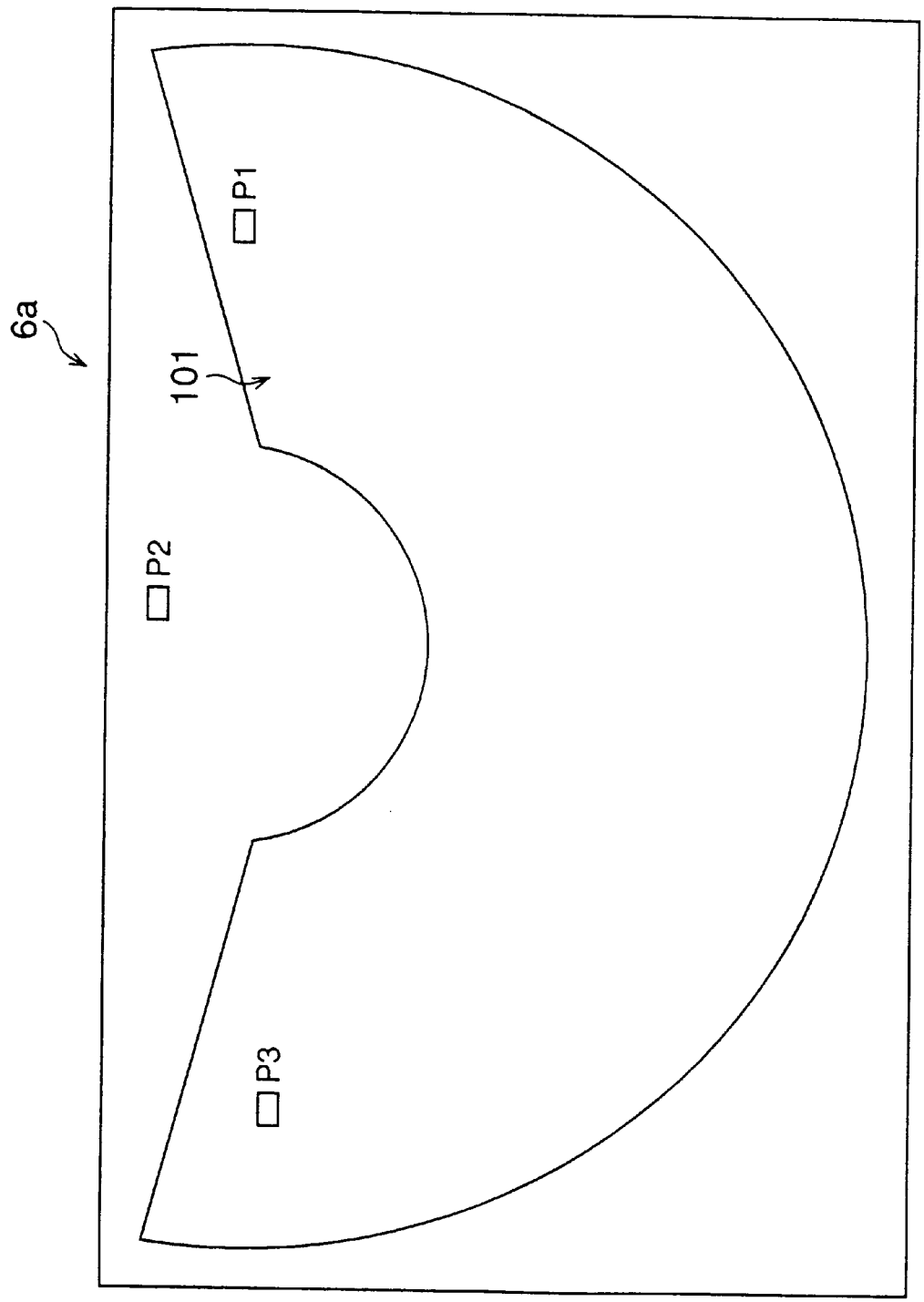
FIG. 5 is an illustration showing, by way of example, images displayed on a display screen, for the purpose of explanation of the fourth embodiment of an ultrasonic diagnostic apparatus according to the present invention.

FIG. 5 is an illustration showing, by way of example, images displayed on a display screen, for the purpose of explanation of the fourth embodiment of an ultrasonic diagnostic apparatus according to the present invention.

On the display screen shown in FIG. 5, there is displayed a largely expanded tomographic image 101. Some type of probe permits such a largely expanded tomographic image to be displayed on the display screen. In a case where the Doppler sample marker is moved from the position of the Doppler sample marker P1 to the position of the Doppler sample marker P3, it is convenient to provide such an arrangement that the field of travelling of the Doppler sample marker is not limited to the inside of the tomographic image 101, and for example, as given by the Doppler sample marker P2, the Doppler sample marker can travel also to the position out of the tomographic image 101. However, in this case, there arises a problem as to where the sample position is set up.

In view of the foregoing, according the fourth embodiment, the Doppler sample marker is permitted to travel to an area out of the tomographic image 101. When the Doppler sample marker travels to an area out of the tomographic image 101, an alteration of the sample position is not performed. When the Doppler sample marker travels again inside the tomographic image 101, an alteration of the sample position is resumed.

Figure 6:
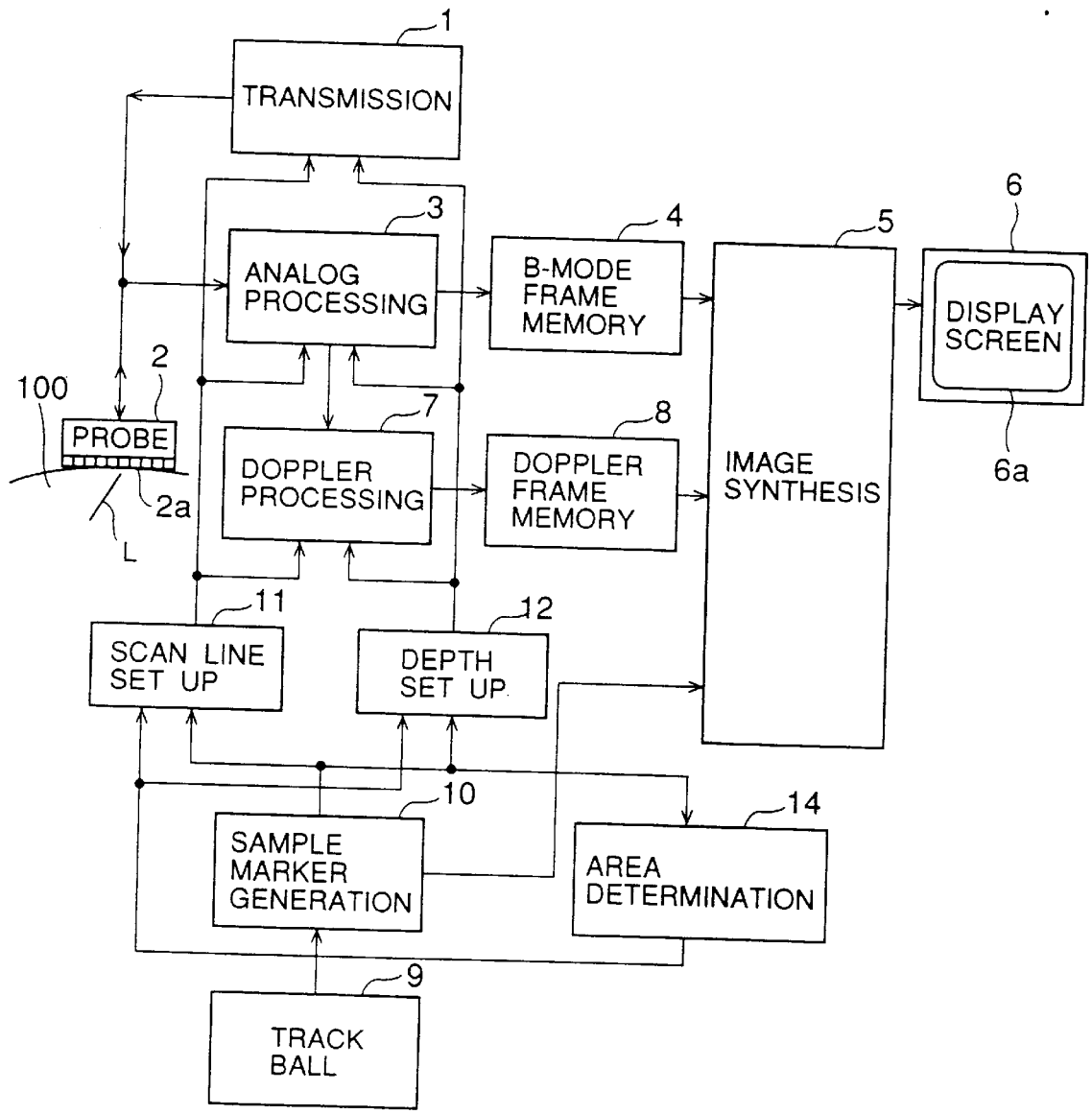
FIG. 6 is a block diagram of an ultrasonic diagnostic apparatus according to the fourth embodiment of the present invention.

FIG. 6 is a block diagram of an ultrasonic diagnostic apparatus according to the fourth embodiment of the present invention. The difference of the fourth embodiment from the first embodiment shown in FIG. 2 will be described hereinafter.

In the ultrasonic diagnostic apparatus according to the fourth embodiment shown in FIG. 6, as compared with the first embodiment shown in FIG. 2, there is added an area determination unit 14. The area determination unit 14 receives indication coordinates of the Doppler sample marker outputted from the sample marker generation unit 10, and determines whether the indication coordinates is within the display area of the tomographic image 101 (FIG. 5) or out of the display area of the tomographic image 101. The area determination unit 14 outputs a signal indicative of whether the Doppler sample marker is within the display area of the tomographic image 101, and transmits the same to the scan line set up unit 11 and the depth set up unit 12. The scan line set up unit 11 and the depth set up unit 12 maintain respectively the previous scan line number and depth during an application of the signal indicating that the Doppler sample marker is out of the display area of the tomographic image 101. When the scan line set up unit 11 and the depth set up unit 12 receives from the area determination unit 14 the signal indicating that the Doppler sample marker returns to the display area of the tomographic image 101, the scan line set up unit 11 and the depth set up unit 12 evaluate respectively scan line number and depth. However, the sample marker generation unit 10 continues to transmit to the image synthesizer unit 5 the signal representative of the figure of the Doppler sample marker, regardless of the operation of the area determination unit 14. And when the track ball 9 is operated, the Doppler sample marker travels on the display screen 6a following an operation of the track ball 9, irrespective of the inside and the outside of the display area of the tomographic image 101.

It is acceptable that the fourth embodiment shown in FIG. 6 is combined with the second embodiment shown in FIG.

3. Specifically, the maker stop determination unit 13 shown in FIG. 3 is added to the fourth embodiment shown in FIG. 6. In this case, even in a case where the Doppler sample marker is within the display area of the tomographic image 101, the sample position is not updated during the travelling of the Doppler sample marker, and the sample position is updated after the Doppler sample marker stops in travelling. Further, it is acceptable that the fourth embodiment shown in FIG. 6 is combined with the third embodiment shown in FIG. 4. In this case, after the sample position is updated, a new Doppler sample marker is drawn at the updated sample position.

Figure 7:
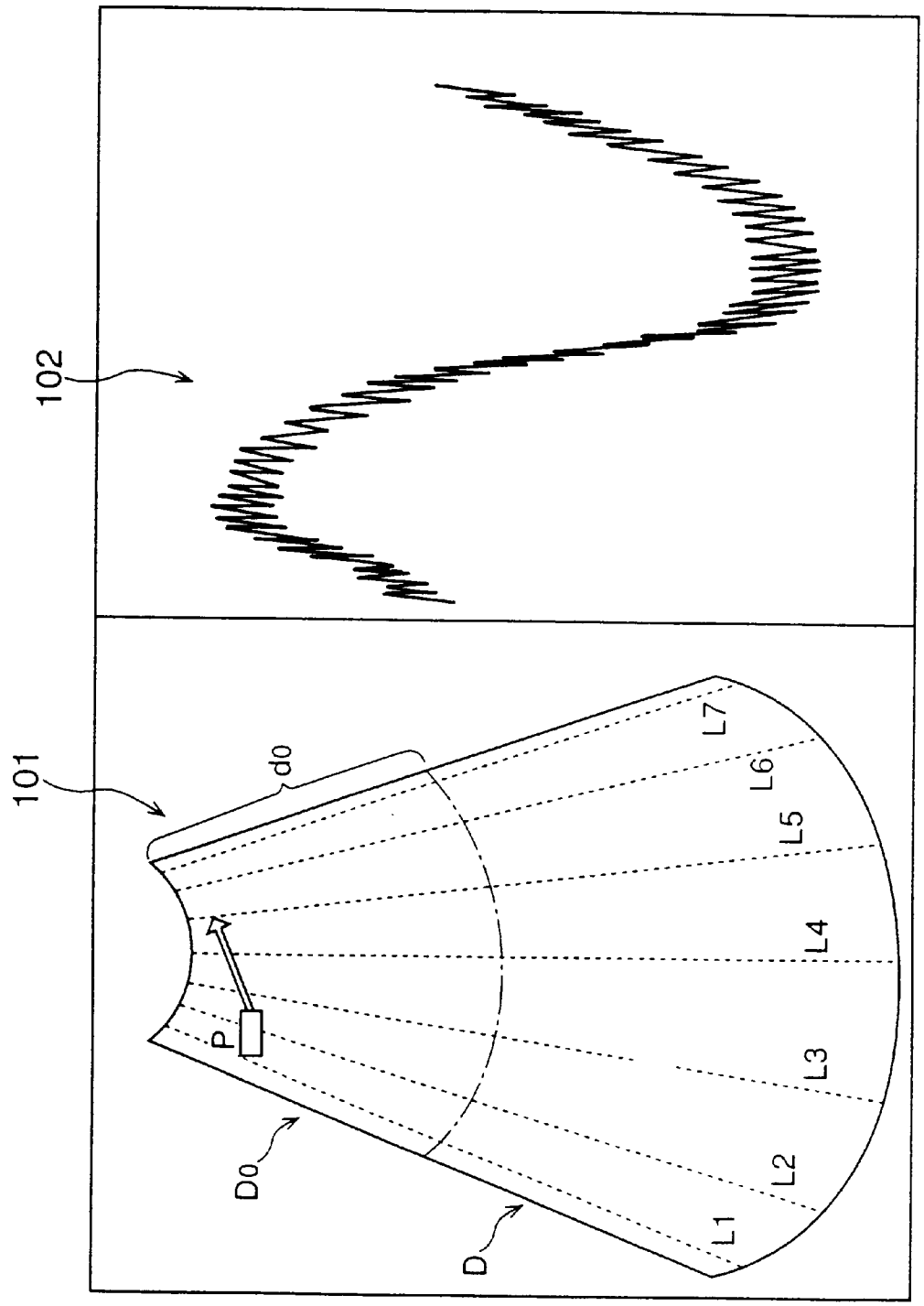
FIG. 7 is an illustration showing, by way of example, images displayed on a display screen, for the purpose of explanation of the fifth embodiment of an ultrasonic diagnostic apparatus according to the present invention.

FIG. 7 is an illustration showing, by way of example, images displayed on a display screen, for the purpose of explanation of the fifth embodiment of an ultrasonic diagnostic apparatus according to the present invention.

A Doppler sample marker P is displayed within an area or domain $D_0$ of the tomographic image 101, which is shallower than a depth $d_0$ corresponding to the shallow portion near the surface of the subject. It is assumed that the track ball is operated so that the Doppler sample marker P is travelled in a direction (horizontal direction) traversing the scan lines. In the domain $D_0$, the scan lines close up. Consequently, when the Doppler sample marker P is travelled in the direction (horizontal direction) crossing the scan lines, a little movement causes the Doppler sample marker P to travel across several scan lines. Thus, in order to travel the Doppler sample marker P to a desired scan line near the current position of the Doppler sample marker P, a fine operation is needed. Then, according to the fifth embodiment, in the event that the Doppler sample marker P is displayed within the domain $D_0$ corresponding to the shallow portion in the subject, when the track ball is operated in such a way that the Doppler sample marker is travelled across the scan lines, the Doppler sample marker is moved sequentially every operation at the position wherein the Doppler sample marker is superposed on the adjacent scan line, regardless of the magnitude of an amount of operation of the track ball. This feature makes it possible to avoid the fine operation thereby improving the operability.

Incidentally, when the Doppler sample marker is within the domain D deeper than the domain $D_0$, the explanation made referring to FIG. 1 is applicable to this case as it is.

Figure 8:
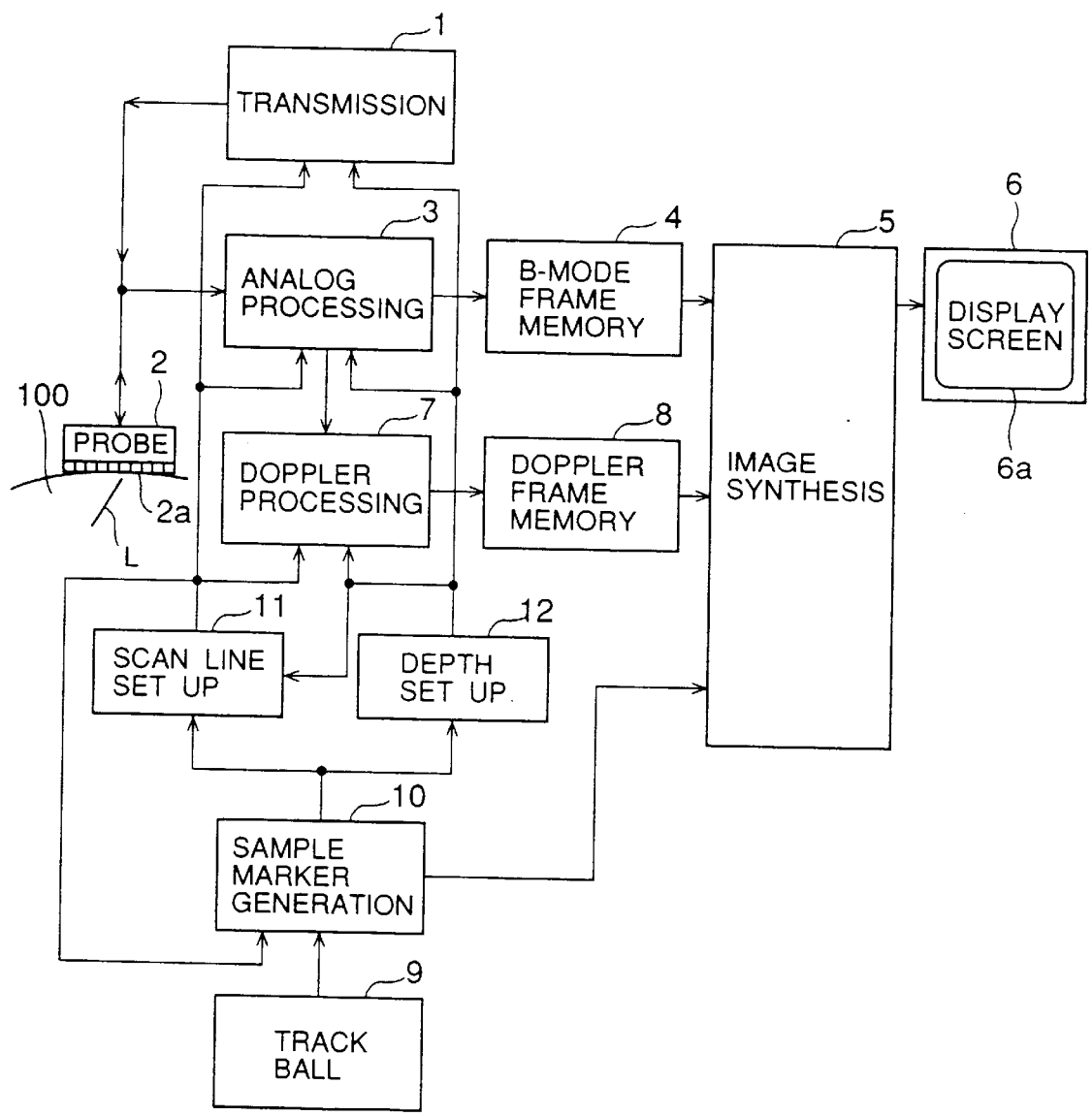
FIG. 8 is a block diagram of an ultrasonic diagnostic apparatus according to the fifth embodiment of the present invention.

FIG. 8 is a block diagram of an ultrasonic diagnostic apparatus according to the fifth embodiment of the present invention.

The sample marker generation unit 10 generates new indication coordinates of the Doppler sample marker in accordance with shift data caused by operation of the track ball 9. However, at that time, such indication coordinates is the provisional indication coordinates, and thus the sample marker generation unit 10 continues to output to the image synthesis unit 5 the figure of the Doppler sample marker having the indication coordinates before a renewal. On the other hand, the scan line set up unit 11 and the depth set up unit 12 receive the provisional indication coordinates after a renewal. The depth set up unit 12 evaluates a depth of the Doppler sample marker indicated by the indication coordinates on the basis of the provisional indication coordinates. The depth thus obtained is fed to the scan line set up unit 11. The scan line set up unit 11 selects a scan line according as a depth of the Doppler sample marker, which is fed from the depth set up unit 12, is within the depth $d_0$ shown in FIG. 7 or not. In the event that the depth of the Doppler sample marker is over the depth $d_0$, in a similar fashion to that of first embodiment shown in FIG. 1, the scan line set up unit 11 selects a scan line closest to the indication coordinates inputted from the sample marker generation unit 10. On the other hand, in the event that the depth of the Doppler sample marker is within the depth $d_0$, a scan line, which is adjacent to the now selected scan line with respect to a direction directed from the now selected scan line to the indication coordinates inputted from the sample marker generation unit 10, is selected. The sample marker generation unit 10 receives a signal indicating what scan line is selected by the scan line set up unit 11. The sample marker generation unit 10 modifies the provisional indication coordinates and decides the same, if necessary, and produces a figure for displaying the Doppler sample marker at the decided indication coordinates and sends the same to the image synthesis unit 5.

Thus, in the event that the Doppler sample marker is displayed within the domain $D_0$ shown in FIG. 7, when it is intended that the track ball 9 is operated to move the Doppler sample marker to another scan line, the Doppler sample marker shifts to the just adjacent scan line every operation, regardless of an amount of operation. Hence, there is no need to control an amount of operation on a fine basis.

Figure 9:
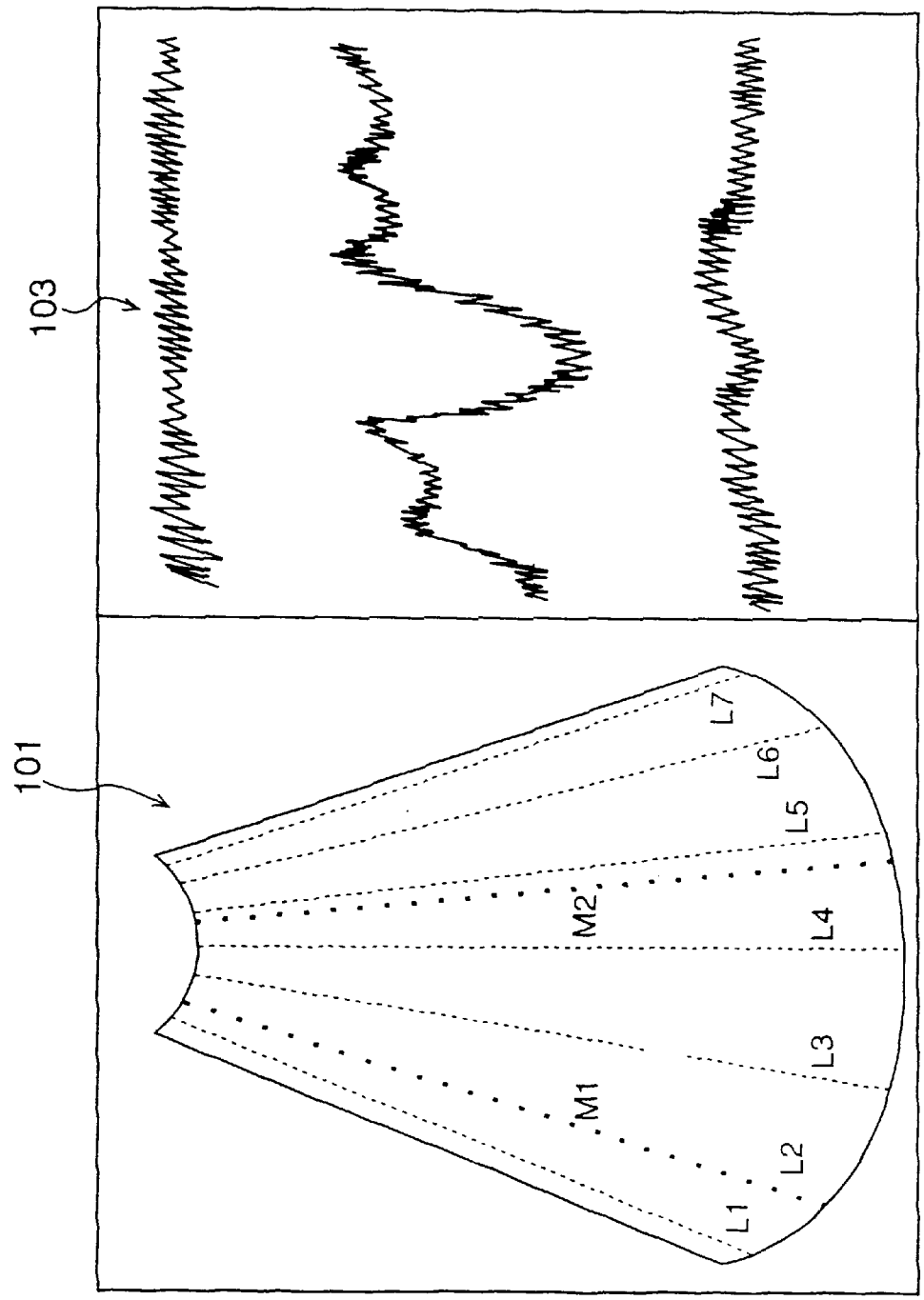
FIG. 9 is an illustration showing, by way of example, images displayed on a display screen, for the purpose of explanation of the sixth to eighth embodiments of an ultrasonic diagnostic apparatus according to the present invention.

FIG. 9 is an illustration showing, by way of example, images displayed on a display screen, for the purpose of explanation of the sixth to eighth embodiments of an ultrasonic diagnostic apparatus according to the present invention.

On the display screen shown in FIG. 1, there are displayed in parallel a black and white of tomographic image 101, and a so-called M-mode image 103 in which a one-dimensional ultrasounds reflection intensity distribution along one scan line selected from among a plurality of scan lines L1 to L7 constituting the tomographic image 101 is expressed by a vertical axis and changes with time of the ultrasounds reflection intensity distribution is expressed by a horizontal axis. The M-mode image 103 is sequentially scrolled with the passage of time. According to this example, the tomographic image 101 corresponds to the two-dimensional image referred to in the present invention, each of the scan lines L1 to L7 corresponds to the processing unit area referred to in the present invention, and a scan line (referred to as an "M direction scan line") selected from among the plurality of scan lines L1 to L7 for a display of the M-mode image corresponds to the noticed area referred to in the present invention.

In the tomographic image 101 shown in FIG. 9, as an M marker for selecting the M direction scan line, the M marker being equivalent to a cursor extended linearly, there are displayed an M marker M1 before a shift and an M marker M2 after a shift. Actually, only one M marker is displayed.

In this case, before a shift the scan line L2 is selected as the M direction scan line, and the M marker M1 before a shift is superposed on the scan line L2. It is assumed that in this condition the M marker shifts to the M marker M2 after a shift. At that time, the M direction scan line is updated from the scan line L2 to the scan line L5 closest to the M marker M2 after a shift.

In this case, as shown in the seventh embodiment which will be described later, it is preferable that the M direction scan line is fixed on the M direction scan line L2 before a shift while the M marker travels, and when the M marker stops at the position of the M marker M2, the M direction scan line shifts from the M direction scan line L2 before a shift to the M direction scan line L5 after a shift. In this case, during a movement of the M marker, as the M-mode image 103, there is continued to be displayed a scroll image representative of an ultrasounds reflection intensity distribution of the M direction scan line L2 before a shift, and after the termination of a movement of the M marker, a scroll image representative of an ultrasounds reflection intensity distribution of the M direction scan line L5 after a shift is displayed.

Further, in this case, as shown in FIG. 9, the M marker M2 after a movement is continued to be displayed at the position out of the M direction scan line L5 after a shift. Then, as shown in the eighth embodiment which will be described later, it is acceptable that after the M marker stops at the position of the M marker M2 and the M direction scan line moves to the M direction scan line L5 shown in FIG. 9, the M marker is shifted to a position at which the M marker is superposed on the M direction scan line L5.

Figure 10:
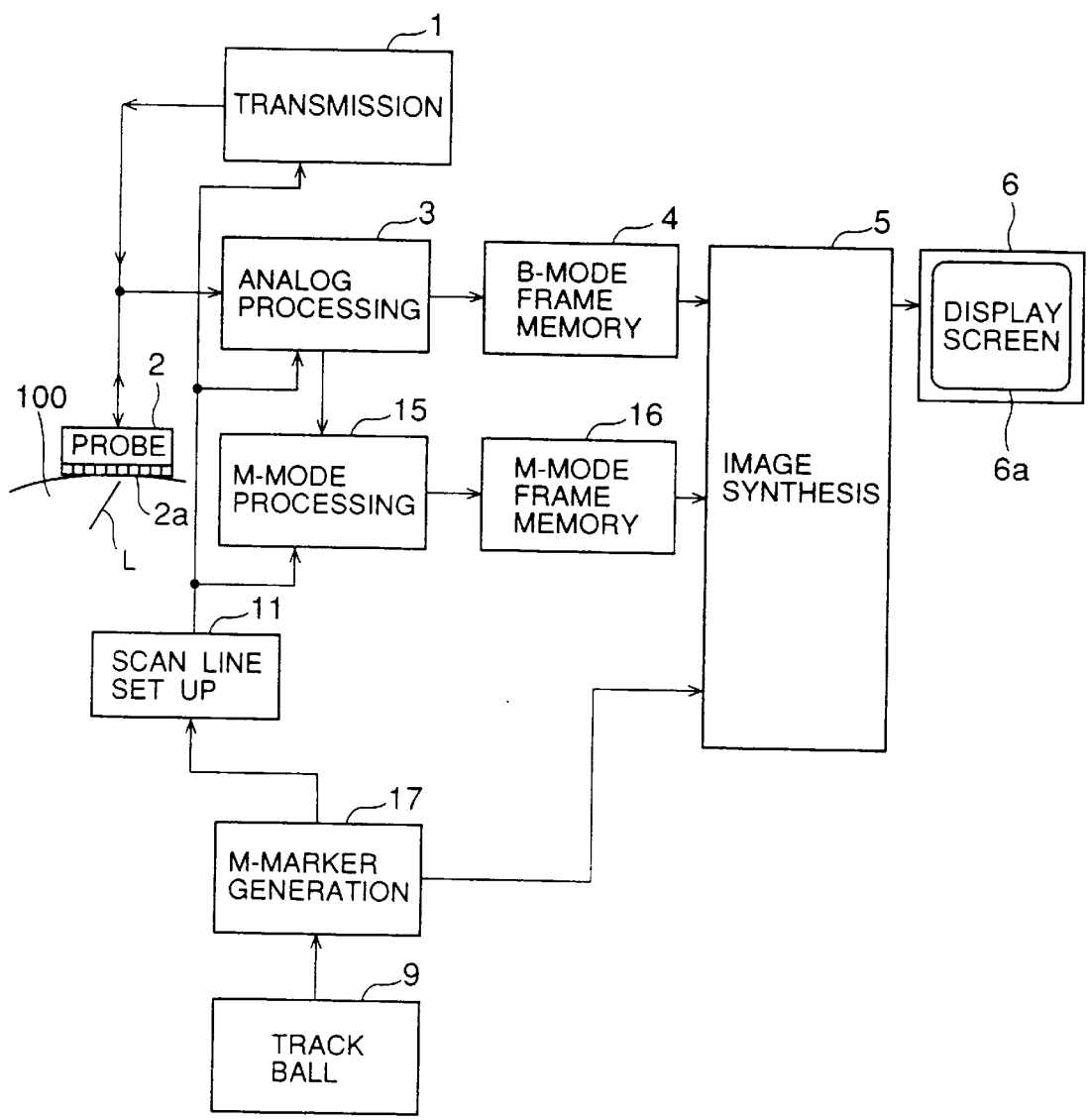
FIG. 10 is a block diagram of an ultrasonic diagnostic apparatus according to the sixth embodiment of the present invention.

FIG. 10 is a block diagram of an ultrasonic diagnostic apparatus according to the sixth embodiment of the present invention. The difference of the sixth embodiment from the first embodiment shown in FIG. 2 will be described hereinafter.

In the sixth embodiment shown in FIG. 10, as compared with the first embodiment shown in FIG. 2, there are provided an M-mode processing unit 15, an M-mode frame memory 16 and a (M marker) generation unit 17, instead of the Doppler processing unit 7, the Doppler frame memory 8 and the M marker generation unit 10. And there is not provided the depth set up unit 12. Incidentally, according to the sixth embodiment shown in FIG. 10, as shown in FIG. 9, the M marker is a linear cursor. Hence, it is sufficient to provide a handler for moving the M marker only in the horizontal direction. Here, however, it is assumed that the track ball 9 in the respective embodiments mentioned above is adopted as it is, and the movement data concerning the vertical direction outputted from the track ball 9 is neglected.

The M-mode processing unit 15 receives a signal immediately after being subjected to the beamforming by the analog processing unit 3. The M-mode processing unit 15 generates a M-mode signal representative of a one-dimensional ultrasounds reflection intensity distribution along the M direction scan line designated in a manner which will be described later. The M-mode signal thus generated is stored in the M-mode frame memory 16. The M-mode signal stored in the M-mode frame memory 16 is read out and fed via the image synthesizer unit 5 to the image display unit 6. In the image display unit 6, the M-mode signal is displayed on the display screen 6a in the form of the M-mode image 103 as shown in FIG. 9 standing side by side with the tomographic image 101.

Next, there will be described a way of setting up or designation of the M direction scan line.

The shift data generated through an operation of the track ball 9 is fed to the M marker generation unit 17. The M marker generation unit 17 evaluates coordinates to be newly displayed on the display screen 6a as to the M marker on the basis of the shift data inputted from the track ball 9 to generate a figure of the M marker to be displayed at the coordinates. The figure of the M marker thus generated is fed to the image synthesizer unit 5.

The indication coordinates of the M marker is not restricted to only the coordinates of the position at which the M marker is superposed on the scan line, and is freely selectable even in position between scan line-to-scan line. The image synthesizer unit 5 transmits the figure of the M marker to the display unit 6 superposing the same on the B-mode image read out from the B-mode frame memory 4.

The display unit 6 displays on the display screen 6a the M marker superposed on the B-mode image. The M marker generation unit 17 outputs the indication coordinates of the M marker, which is fed to a scan line set up unit 11. In the present embodiment, the scan line set up unit 11 correspond to the processing control means referred to in the present invention. The scan line set up unit 11 selects the scan line closest to the indication coordinates as the M direction scan line in accordance with indication coordinates information of the M marker transmitted from the M marker generation unit 17. Information as to the scan line obtained by the scan line set up unit 11, which represents which scan line is selected as the M direction scan line, is fed to the transmission unit 1, the analog processing unit 3 and the M-mode processing unit 15. The transmission unit 1, the analog processing unit 3 and the M-mode processing unit 15 perform an ultrasound transmission processing suitable for the selected M direction scan line, a beamforming processing and a B-mode signal generation processing.

Figure 11:
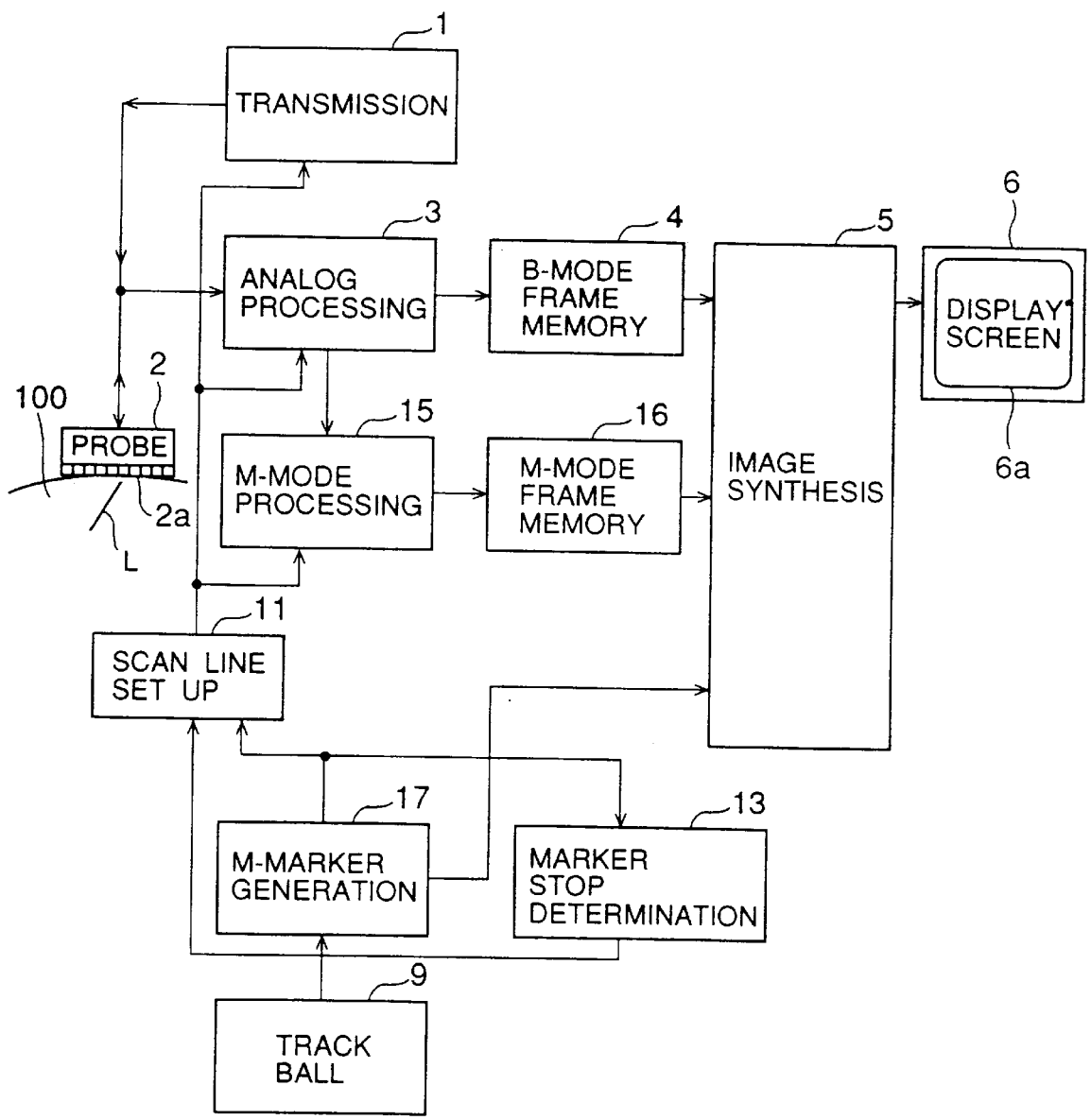
FIG. 11 is a block diagram of an ultrasonic diagnostic apparatus according to the seventh embodiment of the present invention.

FIG. 11 is a block diagram of an ultrasonic diagnostic apparatus according to the seventh embodiment of the present invention. The difference of the seventh embodiment from the sixth embodiment shown in FIG. 10 will be described hereinafter.

In the seventh embodiment shown in FIG. 11, as compared with the sixth embodiment shown in FIG. 10, there is provided a marker stop determination unit 13. The marker stop determination unit 13 receives the indication coordinates of the M marker outputted from the M marker generation unit 17. Upon receipt of the indication coordinates, the marker stop determination unit 13 monitors changes of the indication coordinates and determines that the M marker stops in travelling when the indication coordinates does not vary for a limited time. The marker stop determination unit 13 outputs a signal indicating whether the M marker is in travelling (the track ball 9 is being operated) or is stopped (the track ball 9 is terminated in operation). This signal is fed to the scan line set up unit 11. The scan line set up unit 11 maintains the previous scan line number during an application of the signal indicating that the M marker is in travelling. When the scan line set up unit 11 receives from the marker stop determination unit 13 the signal indicating that the M marker is stopped in travelling, the scan line set up unit 11 evaluates a new M direction scan line number in accordance with the indication coordinates of the M marker which is received from the M marker generation unit 17 at that time. However, the M marker generation unit 17 continues to transmit to the image synthesizer unit 5 the signal representative of the figure of the M marker, regardless of the operation of the marker stop determination unit 13, even while the track ball 9 is operated. In other words, when the track ball 9 is operated, the M marker travels on the display screen 6a following an operation of the track ball 9, but a change of the M direction scan line is carried out after the termination of the operation of the track ball 9.

Figure 12:
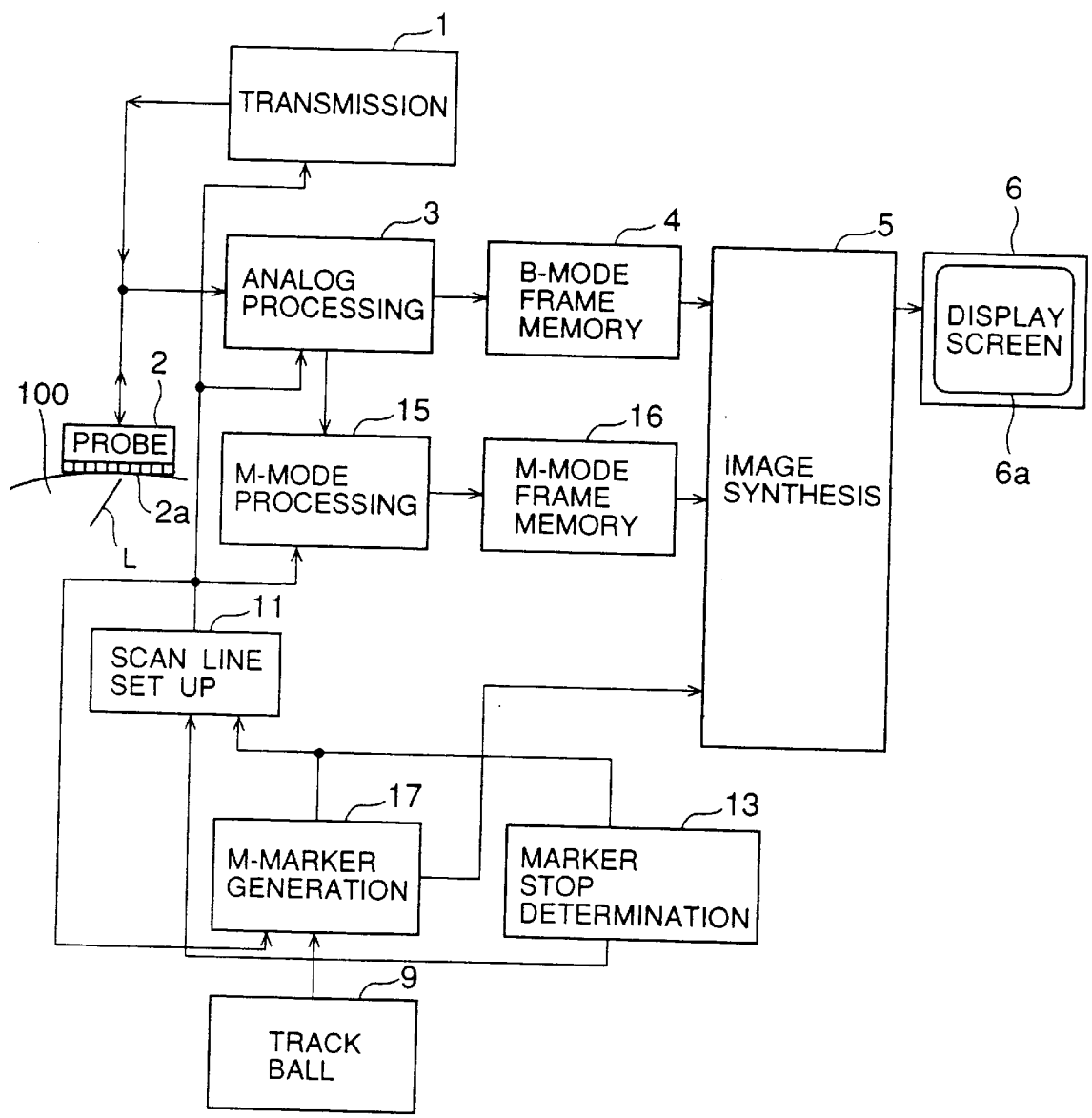
FIG. 12 is a block diagram of an ultrasonic diagnostic apparatus according to the eighth embodiment of the present invention.

FIG. 12 is a block diagram of an ultrasonic diagnostic apparatus according to the eighth embodiment of the present invention. The difference of the eighth embodiment from the seventh embodiment shown in FIG. 11 will be described hereinafter.

Upon receipt of detection of the stop (termination of the operation of the track ball 9) of the M marker by the marker stop determination unit 13, when the scan line set up unit 11 determines a new M direction scan line, the signal representative of the new M direction scan line is fed to the M marker generation unit 17. Upon receipt of such a signal representative of the new M direction scan line, the M marker generation unit 17 updates the M marker at the position in which the M marker is superposed on the M direction scan line indicated by the signal received. This feature makes it possible to avoid such a situation that the M marker is continued to be displayed out of the M direction scan line.

Next, again referring to FIGS. 9 to 12, there will be described the ninth to eleventh embodiments according to the present invention.

According to the ninth to eleventh embodiments, the M-mode image 103 shown in FIG. 9 is considered as a so-called color M-mode image in which blood flow information on one-dimensional respective point along the M direction scan line is indicated in such a manner that a blood flow of direction coming near the probe (the surface of the subject) end and a blood flow of direction going away from the probe (the surface of the subject) are displayed with red and blue, respectively, and the magnitude of the blood flow is expressed with luminance of the thus given red and blue and changes with time is expressed on the axis of abscissas. In this case, The M-mode processing unit 15 shown in FIGS. 10 to 12 is replaced by a color M-mode processing unit. The others are the same as the above-mentioned sixth to eighth embodiments. When the embodiments shown in FIGS. 10 to 12 are modified in accordance with such a replacement, the modified embodiments form the ninth to eleventh embodiments. Redundant explanation will be omitted.

Next, further again referring to FIGS. 9 to 12, there will be described the twelfth to fourteenth embodiments according to the present invention.

According to the twelfth to fourteenth embodiments, the M-mode image shown in FIG. 9 is replaced by a CWD (Continuous Wave Doppler) image representative of an average blood information on a scan line using overall signals associated with the scan line in its entirety. This CWD image is analogous to the Doppler image 102 shown in FIG. 1 rather than the M-mode image 103 shown in FIG. 9.

Further, according to the twelfth to fourteenth embodiments, the M-mode processing unit 15 shown in FIGS. 10 to 12 is replaced by a CWD processing unit for generating a CWD signal representative of the CWD image. The others are the same as the above-mentioned sixth to eighth embodiments. When the embodiments shown in FIGS. 10 to 12 are modified in accordance with such a replacement, the modified embodiments form the twelfth to fourteenth embodiments. Redundant explanation will be omitted.

Finally, referring to FIGS. 1 to 4, there will be described the fifteenth to seventeenth embodiments according to the present invention.

When the above-mentioned CWD image is generated, a focal point for transmission and reception of ultrasounds is designated on the tomographic image 101. Then, it is assumed that the Doppler sample marker P1 and P2 in FIG. 1 are each a focus marker, and the focal point is shifted from a focus S1 to a focus S2. In this case, there is provided a focus marker generation unit for generating an indication coordinates of the focus marker and a figure of the focus marker, instead of the sample marker generation unit 10 in FIGS. 2 to 4. And the transmission unit 1 and the analog processing unit 3 control the transmission of ultrasounds and the signal delay for the beamforming so that a focus is formed on the scan line and the depth designated respectively by the scan line set up unit 11 and the depth set up unit 12. Further, according to the fifteenth to seventeenth embodiments, the Doppler processing unit 7 shown in FIGS. 2 to 4 is replaced by the above-mentioned CWD processing unit. When the embodiments shown in FIGS. 2 to 4 are modified in accordance with such a replacement, the modified embodiments form the fifteenth to seventeenth embodiments. Redundant explanation will be omitted.

As shown in the above-mentioned various types of embodiments, the present invention has various uses in an ultrasonic diagnostic apparatus.

Incidentally, according to the above-mentioned various types of embodiments, there is used the track ball 9 as the handler referred to in the present invention. It is acceptable, however, that anther type of handler, for example, an mouse and the like, is adopted. In the event that the mouse is adopted, it is acceptable to provide such a control that a cursor is moved while a mouse button is depressed (a so-called drag operation), and when the mouse button is released, it is determined that the cursor stops in travelling.

As mentioned above, according to the present invention, it is possible to perform a cursor display suitable to a feeling of handling.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

I claim:

1. An ultrasonic diagnostic apparatus comprising:

an ultrasonic transmitter-receiver sequentially repeating a transmitting-receiving operation on a plurality of scan lines extending within a subject, for each scan line the transmitting-receiving operation comprising transmitting ultrasound in a direction along the scan line;

receiving signals formed by ultrasound reflected from respective points on the scan line;

an image generator generating an image signal carrying image information on a tomographic plane within the subject in accordance with the received signals, the tomographic plane being formed by the plurality of scan lines;

an image display having a display screen displaying a two-dimensional image based on the image signal;

a processing controller selecting as a noticed area a processing unit area included in one of a first plurality of processing unit areas each corresponding to an associated one of said plurality of scan lines and a second plurality of processing unit areas formed by partitioning an associated one of said plurality of scan lines into a plurality of segments, said processing controller controlling at least one of said ultrasonic transmitter-receiver, said image generator, and said image display based on the noticed area;

a cursor display controller controlling display of a cursor for designating the noticed area from among the processing unit areas, the cursor being displayed on the display screen of said image display; and a handler inputting an indication of a display position of the cursor on the display screen of said image display;

wherein said cursor display controller controls display of the cursor at the display position based on the indication input by said handler, the display position being selected from a plurality of positions including a position superposed on a specified processing unit area of the two-dimensional image and further including a position outside every processing unit area; and wherein the processing unit area selected by said processing controller as the noticed area is a processing unit area close to the display position of the cursor.

2. An ultrasonic diagnostic apparatus according to claim 1, wherein said processing controller maintains the noticed area when said handler indicates travel of the cursor on the display screen, and said processing controller selects another processing control unit as the noticed area when the cursor has stopped travelling.

3. An ultrasonic diagnostic apparatus according to claim 2, wherein said cursor display controller shifts the cursor on the display screen to a position superposed on the noticed area when said processing controller selects the noticed area.

4. An ultrasonic diagnostic apparatus according to claim 1, wherein said cursor display controller controls display of the cursor based on the indication input by said handler, the display position being selected from a plurality of positions including a position superposed on a specified processing unit area of the two-dimensional image displayed on the display screen, a position outside every processing unit area on the two-dimensional image, and a position outside a display area of the two-dimensional image; and wherein said processing controller maintains as the noticed area a processing unit area within the display area of the two-dimensional image when said handler indicates a display position outside the display area on the two-dimensional image, and when the cursor of the display screen shifts into the display area of the two-dimensional image, said processing controller selects another processing unit area as the noticed area.

5. An ultrasonic diagnostic apparatus according to claim 1, wherein:

when the noticed area is selected from among the second plurality of processing unit areas and the cursor is displayed on the two-dimensional image within a predetermined shallow area corresponding to a shallow portion of the subject, then said cursor display controller controls display of the cursor to be superposed successively on a series of adjacent scan lines when the handler indicates travel of the cursor in a direction traversing the plurality of scan lines.

6. An ultrasonic diagnostic apparatus according to claim 1, wherein:

said image generator produces a Doppler image representative of time variations of blood flow in the noticed area;

said processing controller selects the noticed area from among the second plurality of processing unit areas and based on the received signals; and said image display displays on the display screen thereof one of the Doppler image and the Doppler image in parallel with the two-dimensional image.

7. An ultrasonic diagnostic apparatus according to claim 1, wherein:

said image generator produces an M-mode image representative of time variations of a one-dimensional ultrasound reflection intensity distribution in the noticed area;

said processing controller selects the noticed area from among the first plurality of processing unit areas based on the received signals; and said image display displays on the display screen thereof one of the M-mode image and the M-mode image in parallel with the two-dimensional image.

8. An ultrasonic diagnostic apparatus according to claim 1, wherein:

said image generator produces a color M-mode image representative of time variations of a one-dimensional blood flow distribution in the noticed area;

said processing controller selects the noticed area from among the first plurality of processing unit areas; and said image display displays on the display screen thereof one of the color M-mode image and the color M-mode image in parallel with the two-dimensional image.

9. An ultrasonic diagnostic apparatus according to claim 1, wherein:

said image generator produces a CWD image representative of time variations of average blood flow in the noticed area;

said processing controller selects the noticed area from among the first plurality of processing unit areas based on the received signals; and said image display displays on the display screen thereof one of the CWD image and the CWD image in parallel with the two-dimensional image.

10. An ultrasonic diagnostic apparatus according to claim 1, wherein:

said ultrasonic transmitter-receiver transmits and receives ultrasound to form a focus in the noticed area; and said processing controller selects the noticed area from among the second plurality of processing unit areas.

* * * * *